United States Patent
Tedesco et al.

(10) Patent No.: US 7,158,225 B2
(45) Date of Patent: Jan. 2, 2007

(54) MULTI-CHANNEL, SELF-CALIBRATING FIBER-COUPLED RAMAN SPECTROMETERS INCLUDING DIAGNOSTIC AND SAFETY FEATURES

(75) Inventors: James M. Tedesco, Livonia, MI (US); Joseph B. Slater, Dexter, MI (US); Kevin L. Davis, Ann Arbor, MI (US); Ronald C. Fairchild, Ann Arbor, MI (US); John W. Baughn, Clinton, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 9 days.

(21) Appl. No.: 10/764,319

(22) Filed: Jan. 23, 2004

(65) Prior Publication Data
US 2005/0162646 A1    Jul. 28, 2005

(51) Int. Cl.
G01J 3/33 (2006.01)
G01J 3/44 (2006.01)
G01N 21/64 (2006.01)
G01N 21/65 (2006.01)

(52) U.S. Cl. ............... 356/301; 356/318; 250/458.1
(58) Field of Classification Search ................ 356/301, 356/317, 318; 250/458.1, 459.1, 461.1, 461.2
See application file for complete search history.

(56) References Cited

U.S. PATENT DOCUMENTS

| | | | |
|---|---|---|---|
| 5,377,004 A | 12/1994 | Owen et al. | 356/301 |
| 5,542,439 A | 8/1996 | Gueret | 132/218 |
| 5,559,557 A | 9/1996 | Kato | 348/405 |
| 5,862,273 A | 1/1999 | Pelletier | 385/12 |
| 5,943,128 A | 8/1999 | Slater | 356/301 |
| 5,963,319 A * | 10/1999 | Jarvis et al. | 356/301 |
| 5,974,211 A | 10/1999 | Slater | 385/33 |
| 6,038,363 A | 3/2000 | Slater et al. | 385/147 |
| 6,259,517 B1 | 7/2001 | Tedesco et al. | 356/73.1 |
| 6,351,306 B1 | 2/2002 | Tedesco et al. | 356/301 |
| 6,603,545 B1 | 8/2003 | Slater | 356/301 |

* cited by examiner

Primary Examiner—F. L. Evans
(74) Attorney, Agent, or Firm—Gifford, Krass, Groh, Sprinkle, Anderson & Citkowski, PC

(57) ABSTRACT

A multi-channel, reconfigurable fiber-coupled Raman instrument uses fiber optic switches for laser and calibration light routing to facilitate automated calibration, diagnosis and operational safety. The system allows wavelength axis calibration on all channels; laser wavelength calibration (including multiple and/or backup laser options); fiber coupling optimization; fault detection/diagnosis; and CCD camera binning setup. In the preferred embodiment, dedicated calibration channels surround data channels on a 2-dimensional CCD dispersed slit image implemented using a unique cabling architecture. This "over/under" calibration interpolation approach facilitates quasi-simultaneous or sequential calibration/data acquisitions. CCD binning between sequential calibration and data acquisitions enables higher density multi-channel operation with tilted images based upon a multiplexed grating configuration. A diamond sample is used as a Raman shift reference for laser calibration, preferably in the form of a small disc sampled with an edge-illuminating probe using two unfiltered fibers.

28 Claims, 19 Drawing Sheets

MULTI-CHANNEL, SELF-CALIBRATING FIBER-COUPLED RAMAN SPECTROMETERS INCLUDING DIAGNOSTIC AND SAFETY FEATURES

FIELD OF THE INVENTION

This invention relates generally to Raman spectroscopy and, more particularly, to multi-channel spectrometers including self-calibrating, diagnostic and safety features.

BACKGROUND OF THE INVENTION

Induced radiative effects such as Raman scattering and fluorescence have become extremely valuable tools associated with the non-destructive determination of molecular constituents. To characterize a composition in a remote or hostile environment, optical fibers may advantageously be used to deliver excitation energy to a sample under investigation and to carry scattered radiation back to instrumentation for spectral analysis. An excitation source path may take the form of a laser providing a stimulus at an appropriate wavelength coupled to an input fiber, and a collection path may be made up of a second fiber carrying return radiative information to a spectral analysis tool such as a spectrograph.

In some instances, laser energy is now transported over relatively long distances via fiber optic cable. Such laser installations are increasingly used in industrial applications for materials processing, process monitoring, and process control. As an example, industrial Raman spectroscopy for chemical process monitoring and control may use laser energy from a laser source installed in a central control room instrument. The instrument couples the laser energy into an optical fiber cable that is routed to a remote probe head. The remote probe head is typically installed into a pipeline that may be hundreds of meters away from the laser source.

Such remote spectral analysis presents technical challenges, however, including the strong scattering signature of the material used for the optical fiber, this interference potentially being generated by both the laser excitation in the illumination fiber and any strong Rayleigh (unshifted) scattering allowed to enter the collection fiber. These spurious fiber signatures can compete with, or even overshadow, the desired signature of the sample under test, particularly when long lengths of fiber are used.

Raman spectroscopy is nevertheless gaining increasing acceptance in on-line process monitoring, due in large part to developments in instrumentation and associated component technologies. For a number of process applications, Raman analyzers have demonstrated significant advantages over alternative techniques such as gas chromatography, IR spectroscopy, and NIR spectroscopy. As a non-destructive, real-time technique, Raman spectroscopy is compatible with a wide variety of samples including opaque solids, aqueous solutions, emulsions, and gases, without the need for sample preparation.

Sampling in a process environment is most conveniently accomplished using a probehead assembly, as shown in the prior-art system of U.S. Pat. No. 5,377,004, incorporated herein by reference. Delivery of the excitation laser beam to the sample under test is accomplished via an excitation fiber-optic cable, and scattered light from the sample is collected by the probehead and routed back to the analyzer via a separate collection fiber-optic cable.

Various optical elements are inserted into the beam delivery path to remove the fiber signature, and the Rayleigh line is typically removed by a notch filter in the collection path. A beam combiner may serve to combine the laser beam delivery path onto a common optical axis with the collection path, so that a common sampling optic may be used for both paths.

Modern Raman instruments may also be configured to monitor multiple sample points in a process. In a typical industrial installation, multiple remote probeheads are coupled to a central instrument via separate fiber optic cables. The central instrument typically houses a laser source, spectrograph, CCD detector and control electronics. A sequencer or splitter 320 is used to multiplex the output of the laser source.

Widespread acceptance of Raman spectroscopy in chemical process monitoring requires accurate and timely instrument calibration. Key parameters to be calibrated in a Raman analyzer include the spectrograph wavelength axis and the laser wavelength itself. Calibration of the spectrograph wavelength axis determines the wavelength versus pixel mapping function of the spectrograph/camera assembly. There are a number of known wavelength calibration sources applicable to Raman spectrometers. Atomic emission lines from readily available neon or argon lamps form convenient wavelength calibration sources. Neon is preferable in that it provides emission lines in close proximity to the common 785 nm and 532 nm laser lines used in process Raman. A neon emission can also provide reference lines near both edges of the CCD for gratings used in certain types of commercially available Raman analyzer equipment.

However, since Raman detection is a frequency-shift phenomenon, wavelength calibration of the spectrograph alone is not sufficient for analyzing Raman shifts with the greatest possible accuracy. Calibrating the wavelength or frequency of the excitation laser source is equally critical. While gas lasers such as helium-neon or argon-ion lasers emit precisely known atomic emission lines, the emission wavelengths of the solid-state lasers more common in process Raman are less stable, and therefore require frequent wavelength calibration.

U.S. Pat. No. 6,351,306, incorporated herein by reference, resides in methods and apparatus for calibrating remote optical probe configurations of the type wherein a spectrum emitted by a sample is delivered to a spectrograph for analysis. The teachings are applicable to various spectroscopic techniques, including fluorescence and Raman detection. Depending upon the embodiment, the system and processes may be used to calibrate the spectrograph wavelength axis, the system spectral response or intensity axis, and the wavelength of the laser used for excitation.

The invention of the '306 patent is applicable to a variety of configurations, including process monitoring environments in which a plurality of probeheads and collection optical fibers are used, each one being associated with a different sample or portion thereof. Nevertheless, particularly in view of recent improvements in optical components and more demanding applications, there remains a constant need for enhancements to systems of this kind, including an ongoing need for multi-channel spectrometers with accurate and automated self-calibrating, diagnostic and safety features.

SUMMARY OF THE INVENTION

This invention resides in a multi-channel, fiber-coupled Raman instrument providing multiple possible configurations using basic building blocks in the form of laser sources, probe heads/optics, fiber switches and other features. Among other novel features, the system makes creative use of fiber optic switches for laser and calibration light routing. Neon light for spectrograph wavelength calibration is injected in a novel way to surround data channels via a novel, multi-channel cabling architecture using industry-standard MTP connectors to provide precision location of several fibers on 250 micron centers. Halogen/incandescent light is used for auto-binning, and photodiodes are placed in multiple locations for system diagnostics and control.

Within the various configurations, automated calibration, diagnosis and safety features are available, including spectrograph wavelength axis calibration on all channels; laser wavelength calibration (including multiple and/or backup laser options); fiber coupling optimization; fault detection/diagnosis; and CCD camera binning setup.

In the preferred embodiment, dedicated calibration channels surround data channels on a 2-dimensional CCD dispersed slit image implemented using a unique cabling architecture. This "over/under" calibration interpolation approach facilitates quasi-simultaneous or sequential calibration/data acquisitions. CCD binning between sequential calibration and data acquisitions enables higher density multi-channel operation with tilted images based upon a multiplexed grating configuration.

Automatic CCD binning setup is possible using a switched broadband light source, and a diamond sample is used as a Raman shift reference for laser calibration. The diamond is preferably in the form of a small disc sampled with an edge-illuminating probe using two unfiltered fibers. Detection of beam transmitted through the diamond reference is also used to optimize laser coupling efficiency with motion servos.

An "intrinsically safe" laser interlock circuit also serves as current source for probe head "laser on" diode indicator. The integrity of key components is monitored through strategically placed photodiodes positioned, for example, at fiber bends to detect light leakage from bent fiber as verification of commanded laser path through fiber switches and at neon and halogen lamp locations to verify lamp operation. The optical switches used for calibration may also be configured for use as a laser shutter.

DETAILED DESCRIPTION OF THE INVENTION

Figure 1:
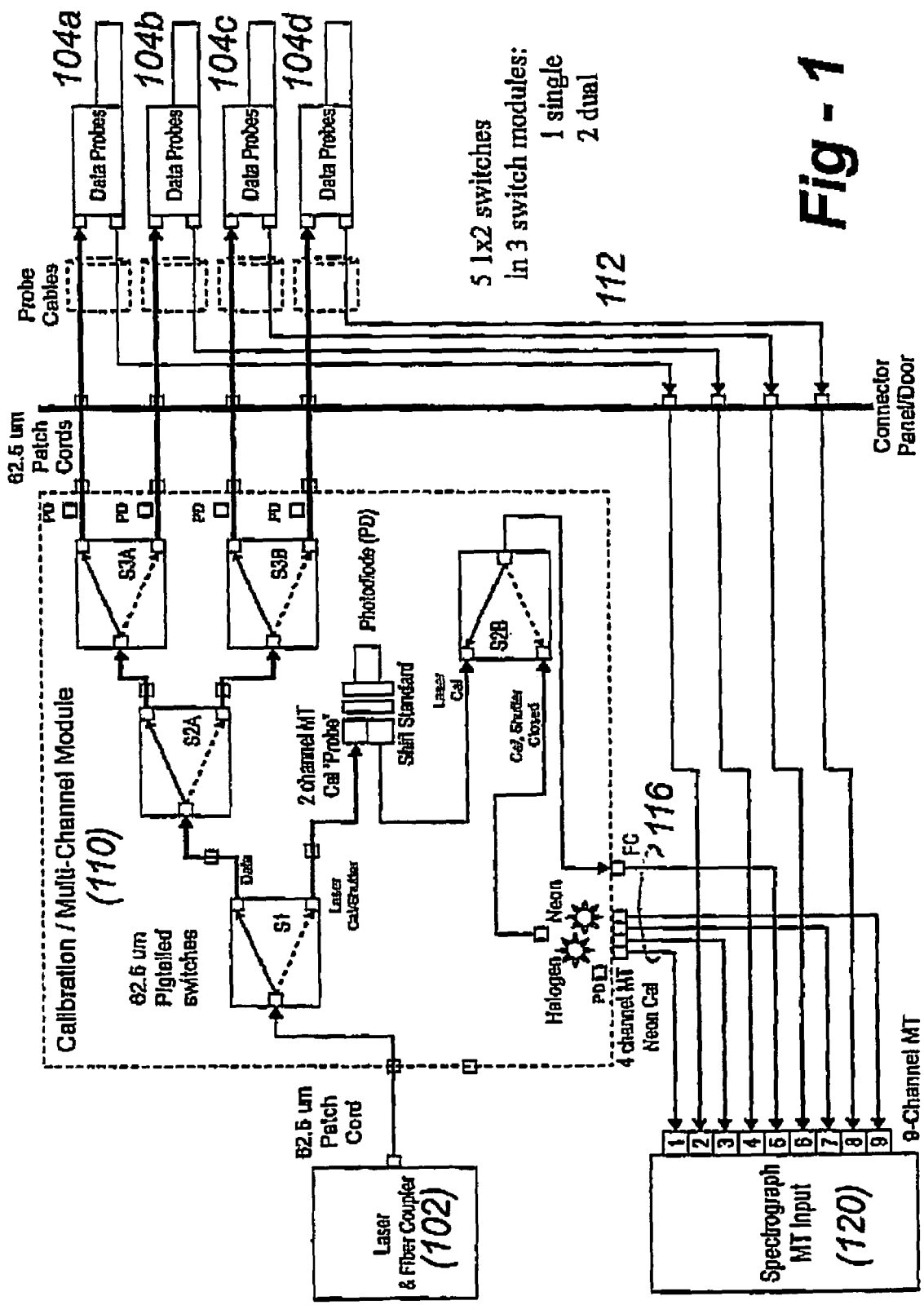
FIG. 1 is a system block diagram of a 1 laser, 4 probe configuration according to the invention.

FIG. 1 is a system block diagram of a 1 laser, 4 probe configuration according to the invention. The laser and fiber coupler is shown at 102, and the probes are shown at 104A through 104D. The probes may use any fiber-coupled type of configuration, including those depicted in U.S. Pat. Nos. 5,377,004; 5,862,273; 5,943,128; 5,974,211; 6,038,363; 6,351,306; and 6,603,545, the entire of content of each being incorporated herein by reference. More particularly, the various filters contained in the probes 104A, 104B, 104C, and 104D may utilize holographic, dielectric, fiber-integrated, and so forth.

The laser 102 and probes 104 are interfaced to a calibration/multi-channel module 110 through optical cables and patch cords. The module 110 in this case includes five low-loss 1×2 optical switches which may be procured from Luminos Industries. The switches, S-1, S-2A, S-3A, S-3B and S-2B route the laser to the data probes and calibration sources, as explained in further detail below. The collection fibers 112 are routed to a 9-channel spectrograph, and the data carried along these fibers is interleaved with five fibers 116, which carry calibration data, as also discussed in further detail below.

Figure 4:
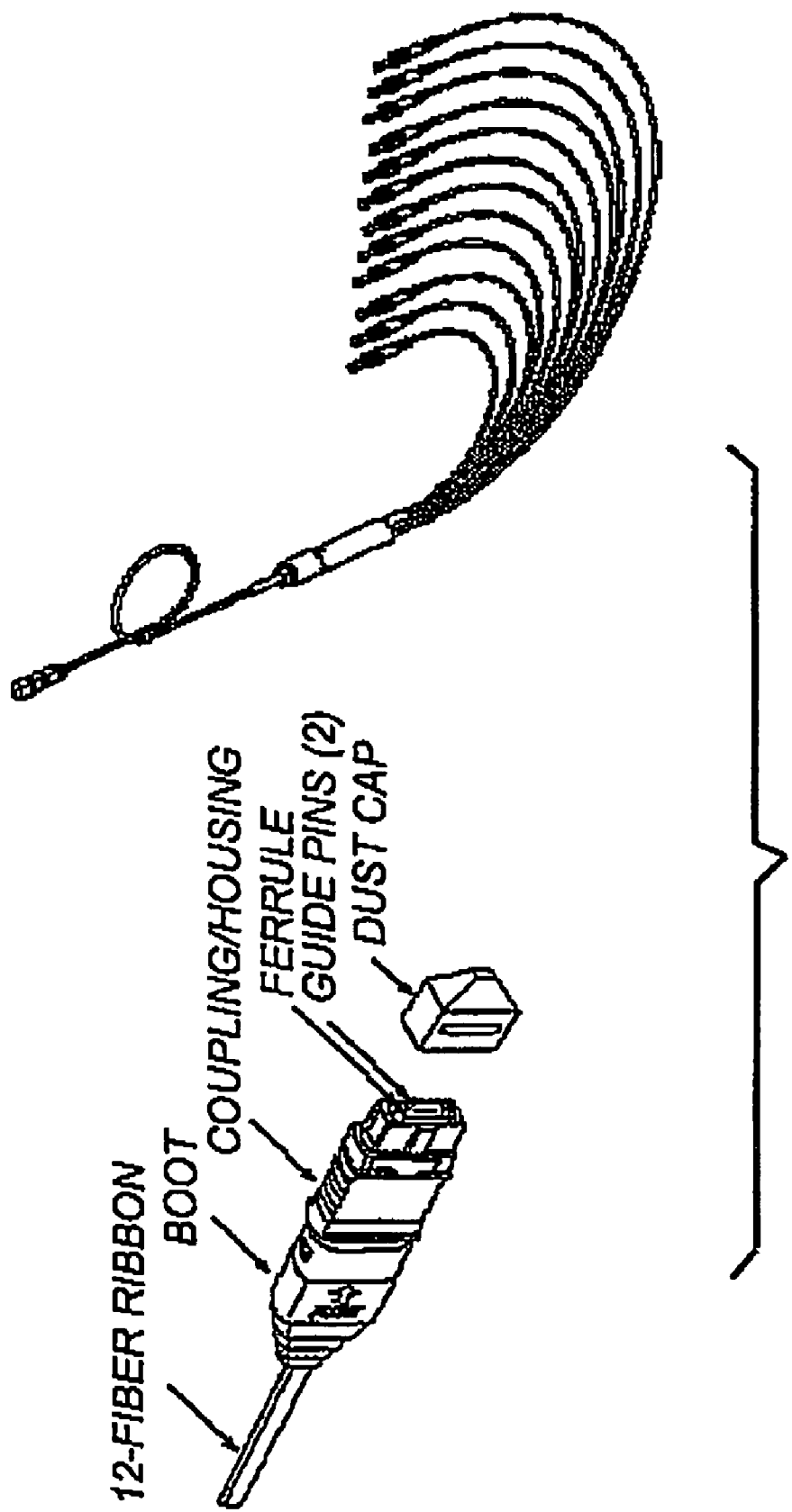
FIG. 4 shows an MTP connector incorporating up to 12 closely spaced optical fibers.

The optical paths are preferably implemented using a unique cabling architecture. FIG. 4 shows an industry standard (i.e., MTP) connector incorporating up to 12 closely spaced optical fibers, enabling the fiber ends to be arranged along the input slit to the spectrograph 120.

Figure 2:
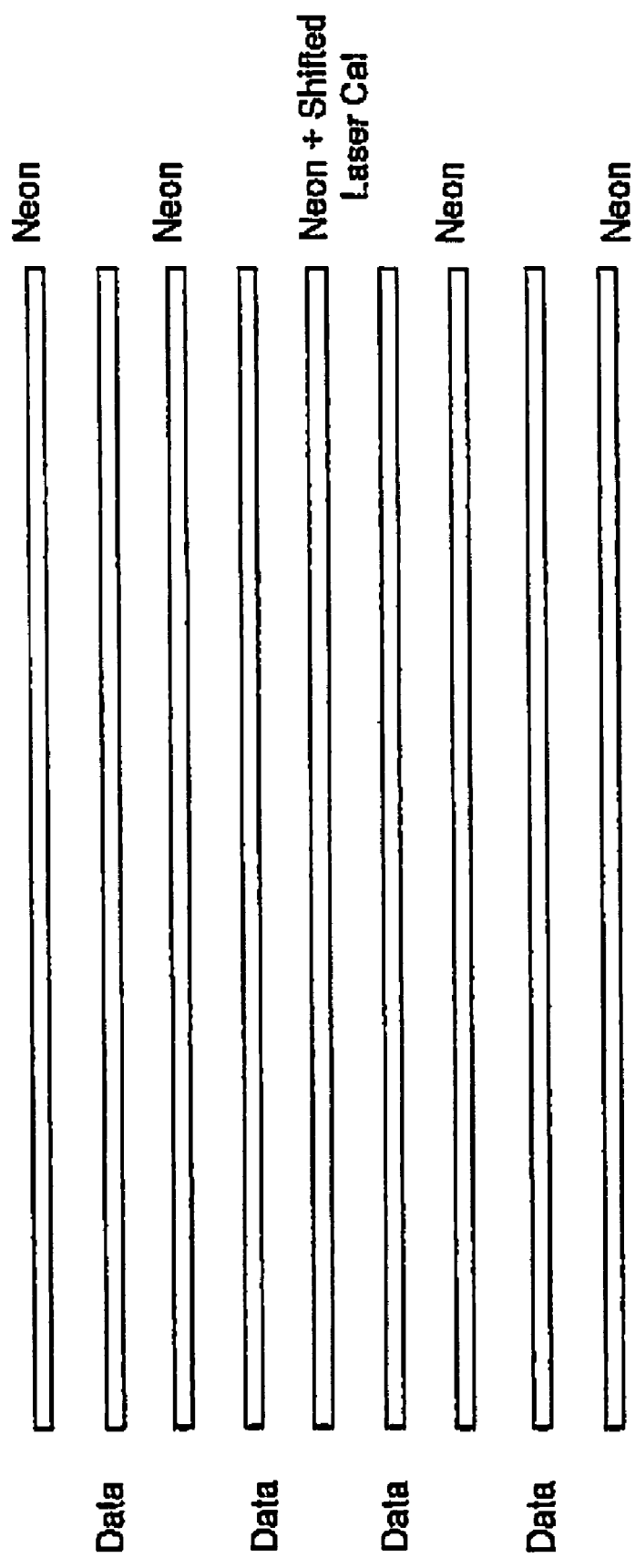
FIG. 2 depicts the CCD image plane of a self-calibrating, 4-channel, single-grating system.
Figure 3:
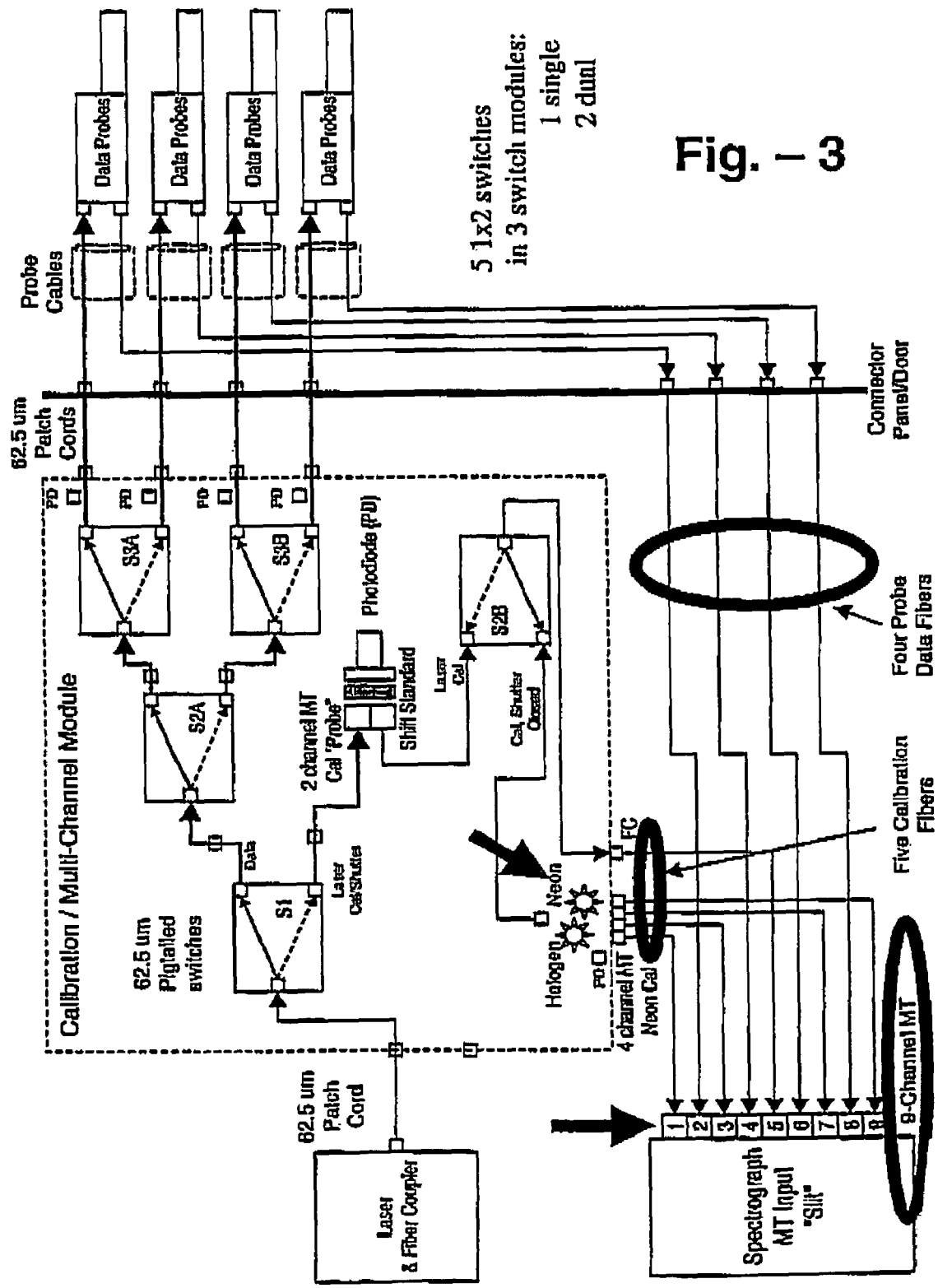
FIG. 3 is a schematic of an optical configuration used to generate interleaved probe data and neon calibration data.

FIG. 3 is a repeat of FIG. 1 with circular call-outs relating to the interleaved probe data and, in this switch configuration, neon calibration data. FIG. 2 depicts how the data and neon channels are arranged on a single grating CCD image plane. To accommodate 4 data channels and 5 calibration channels, a nine-fiber MT is required; additional data channels may be accommodated with a 12-fiber MT, for example. To improve range or resolution, a multiplexing arrangement is preferred of the types described in U.S. Pat. Nos. 5,442,439 or 5,559,597, the content of both being incorporated herein by reference. However, with the configuration shown in FIG. 2, there is not enough area on the CCD to multiplex without shifting binning between data and calibration acquisitions.

Figure 5:
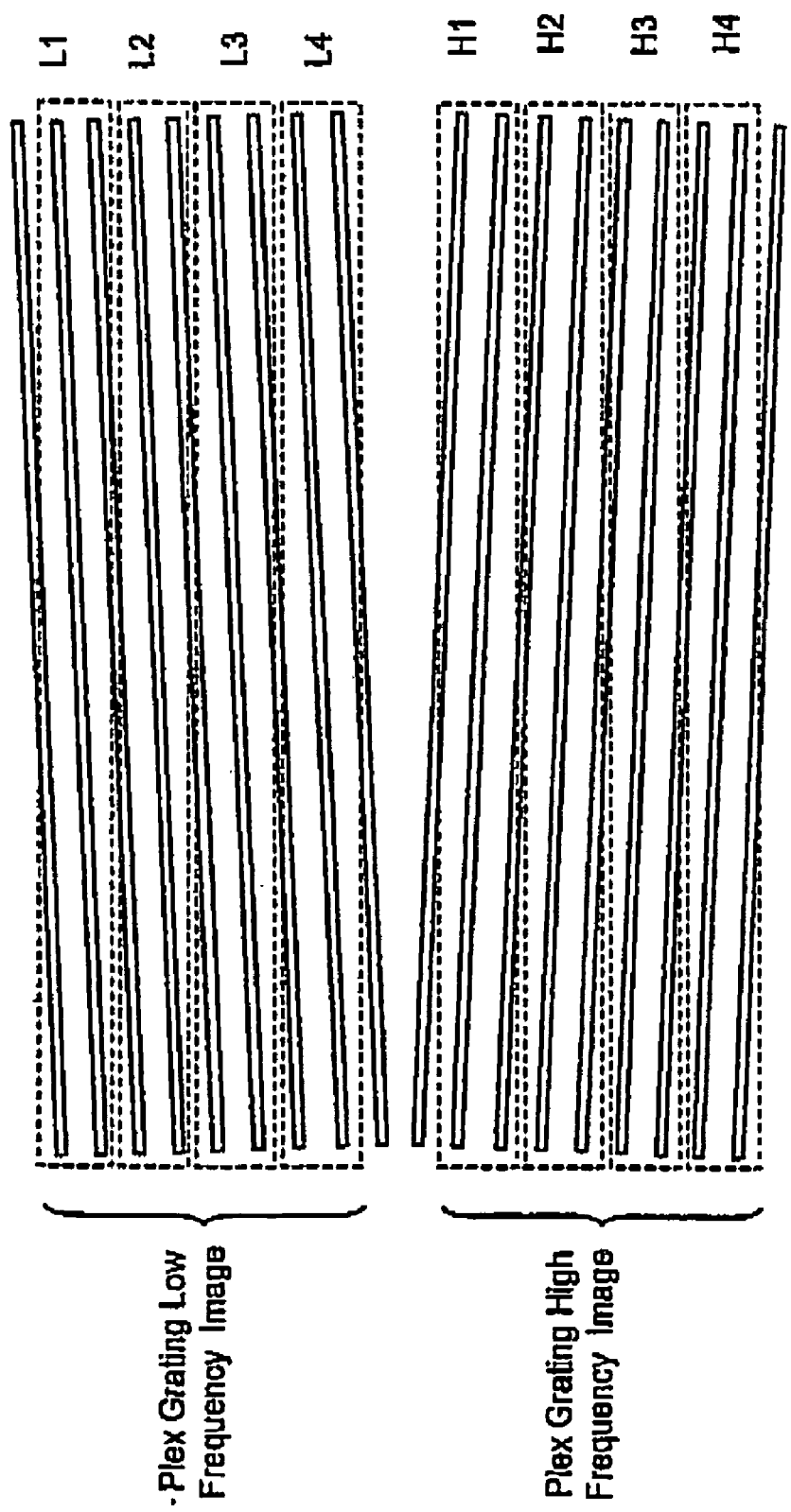
FIG. 5 illustrates 4-channel data binning in conjunction with a multiplexed grating CCD image plane.
Figure 6:
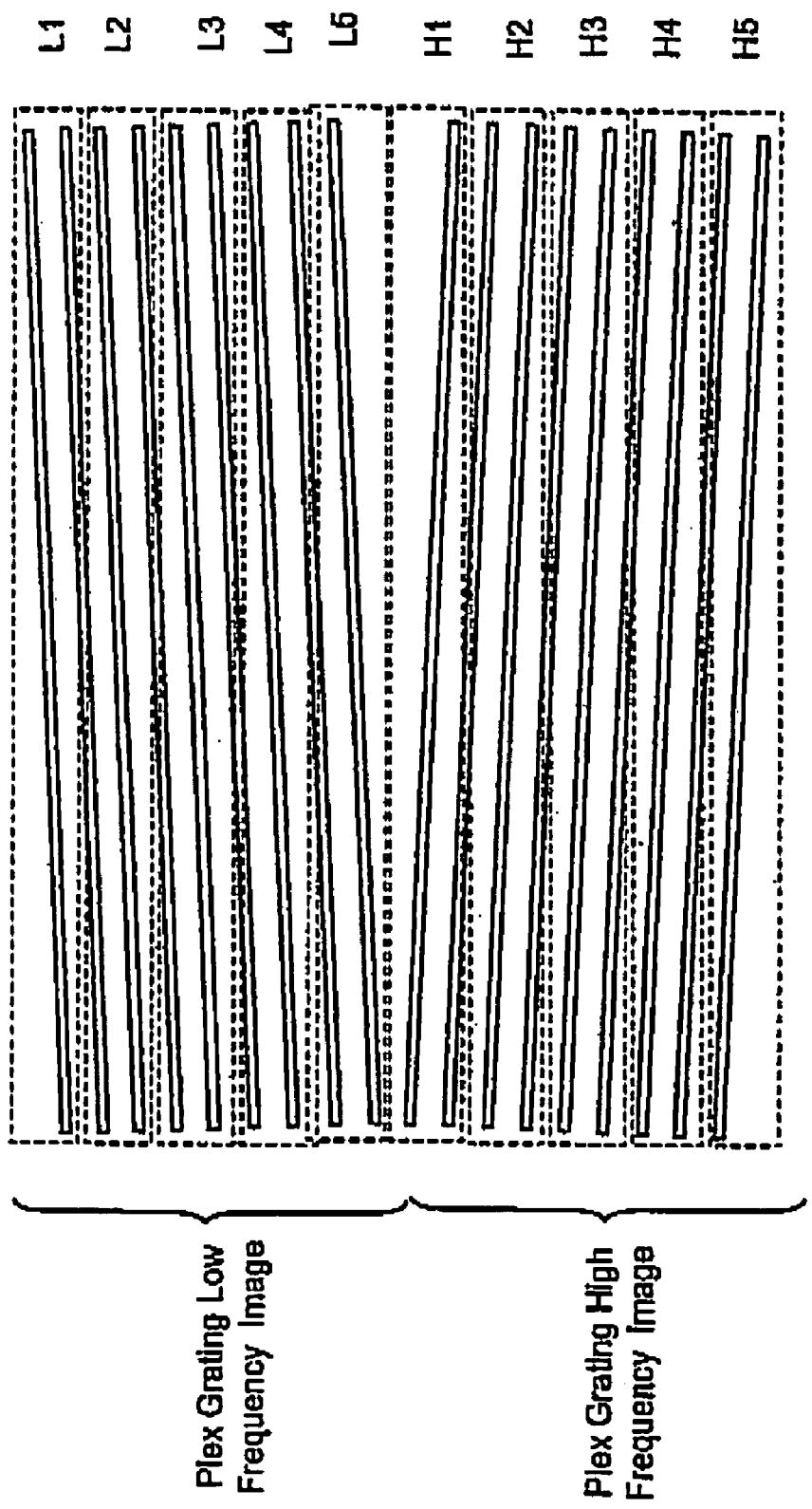
FIG. 6 illustrates 5-channel calibration binning in conjunction with a multiplexed grating CCD image plane.

Accordingly, shift binning is used for both low-frequency and high-frequency grating types. FIG. 5 illustrates a 4-channel data binning arrangement in conjunction with a multiplexed grating CCD image plane, and FIG. 6 illustrates 5-channel calibration binning. Note that no light impinges on the data channels when calibrating, and vice versa.

The redefinition of CCD binning between sequential calibration and data acquisitions enables higher-density multi-grating (or multi-channel, multi-grating) operation with tilted images. The dedicated calibration channels also "surround" the data channels on 2D CCD dispersed slit image, facilitating an "over/under" calibration interpolation approach. The approach to the calibration/data acquisitions may either be quasi-simultaneous or sequential.

Figure 18:
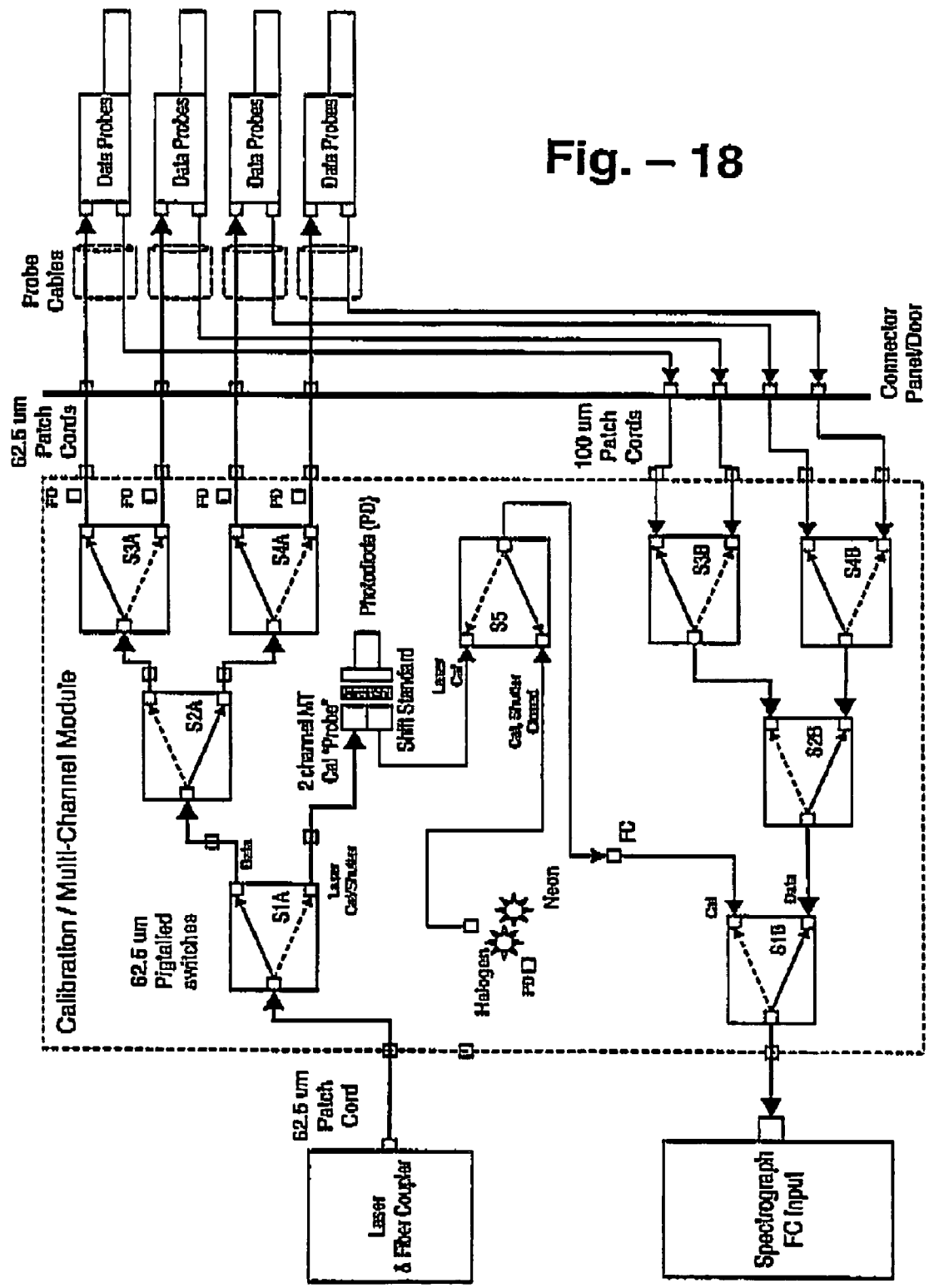
FIG. 18 is a diagram depicting the use of switches from multiple probe collection fibers facilitating the use of a smaller imager and more direct calibration.

Although, as depicted in FIG. 18, optimal calibration is achieved by feeding calibration light through the data fiber (s) to the data-collecting detectors, this embodiment of the invention compromises by interpolating calibrations on immediately surrounding channels. Although many interpolation algorithms are possible, experimental results have shown that a simple linear interpolation agrees with an optimal approach to less than ~0.05 pixel rms (~0.1 cm-1) for worst-case multiplexed grating implementation. The design corrects for camera tilt/yaw, slit image curvature, lens distortion, an so forth, and is therefore more accurate than a single-neon channel approach which assigns one calibration curve to the entire array.

FIG. 8 illustrates actual CCD camera images corresponding to the calibration binning of FIG. 6 and the data binning of FIG. 5. FIGS. 8 and 9 also illustrate a different aspect of the invention involving an automatic CCD binning setup using an internal, switched broadband light source such as the halogen lamp 130 of FIG. 1.

Figure 7:
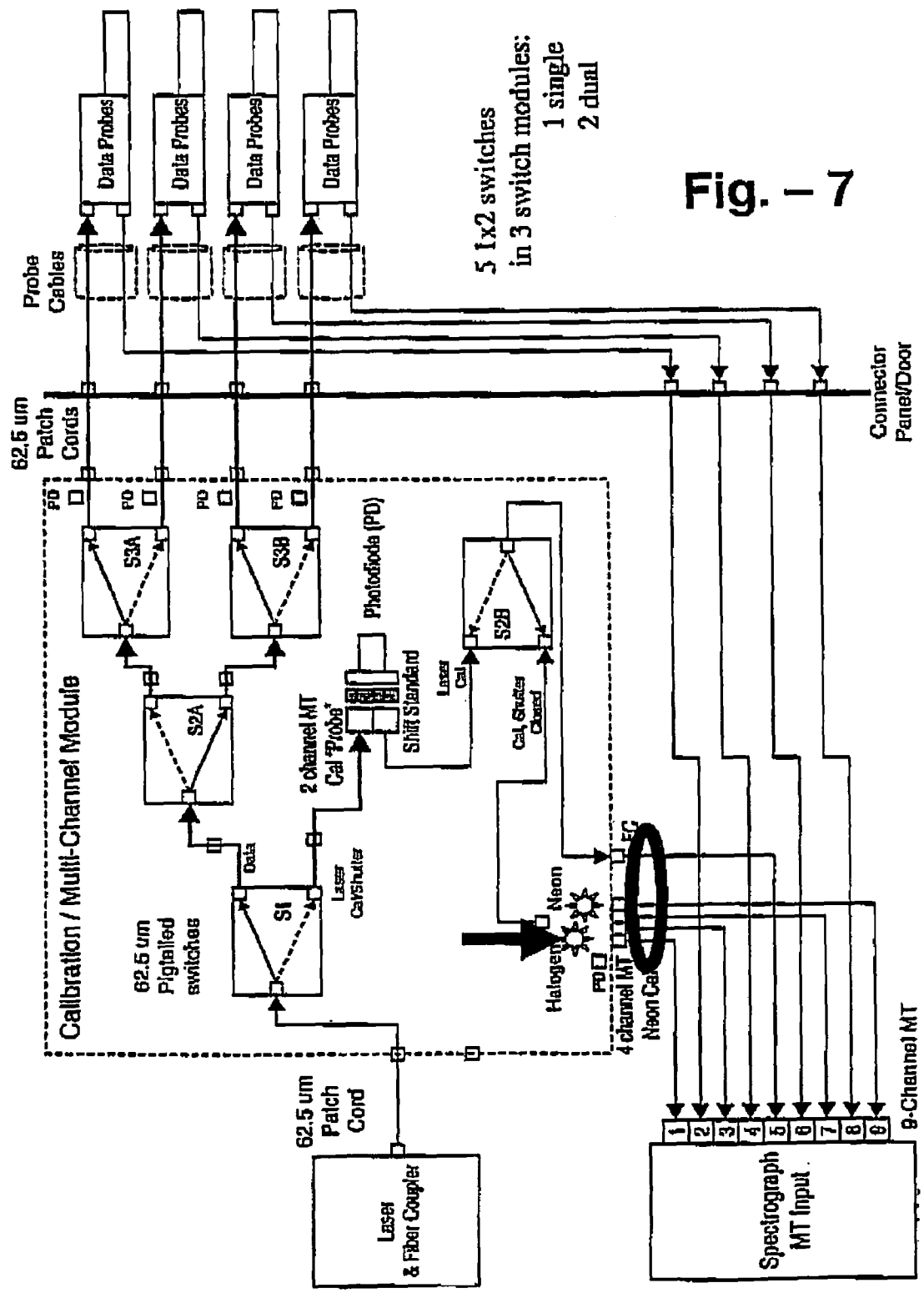
FIG. 7 depicts the use of a broadband source for CCD auto-binning.
Figure 8A:
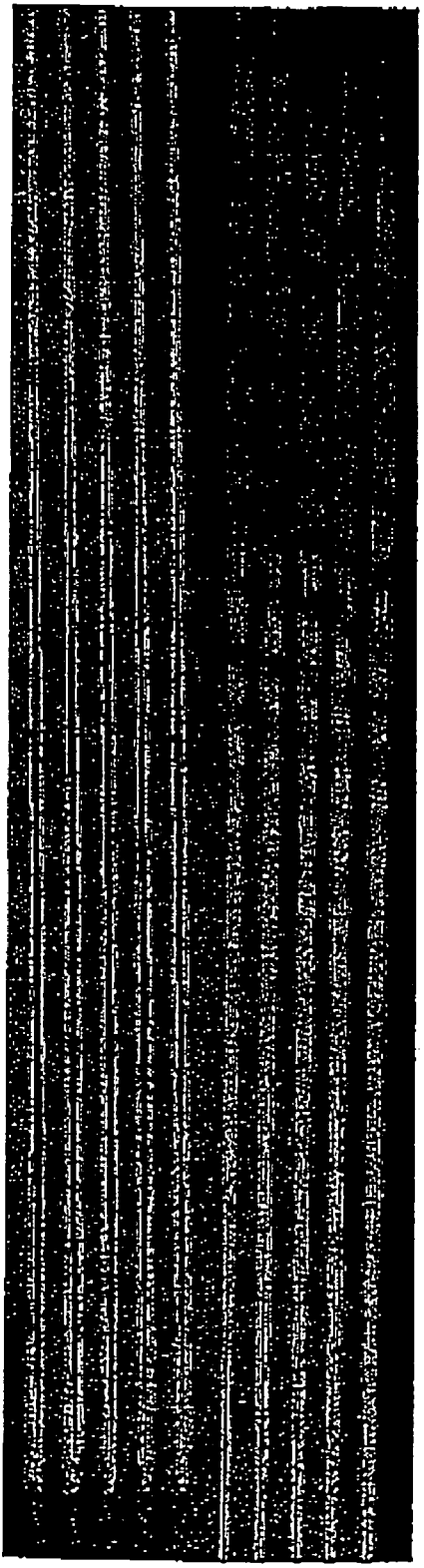
FIG. 8A shows an auto-binning camera image with 5 calibration channels illuminated.
Figure 8B:
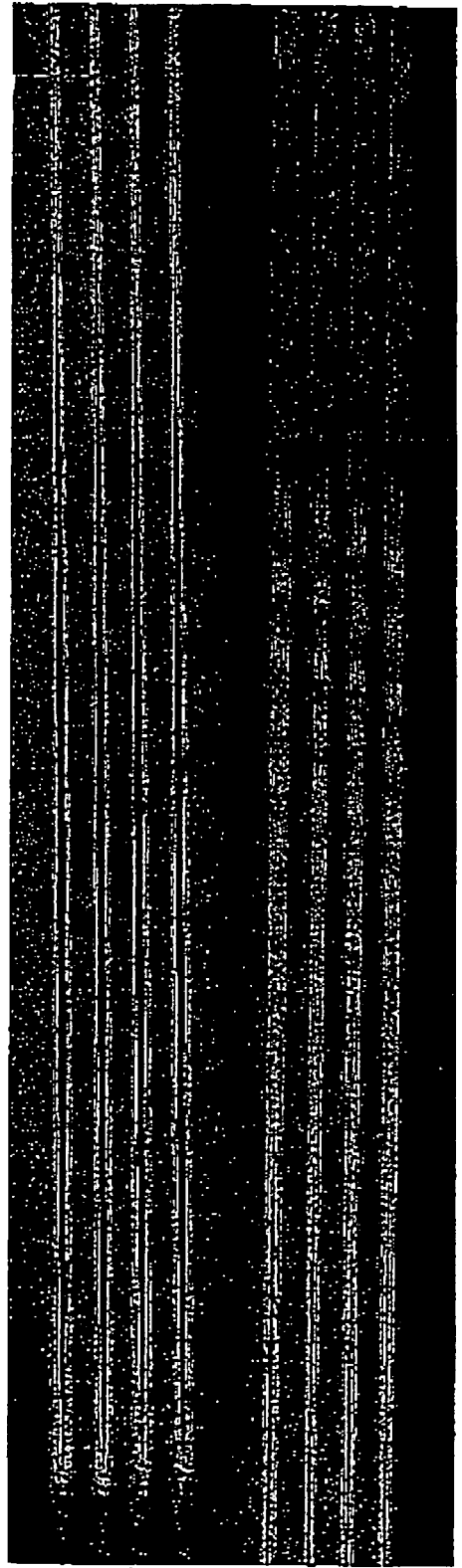
FIG. 8B shows how the auto-binning of 4 data channels bisects 5 calibration channels.
Figure 9:
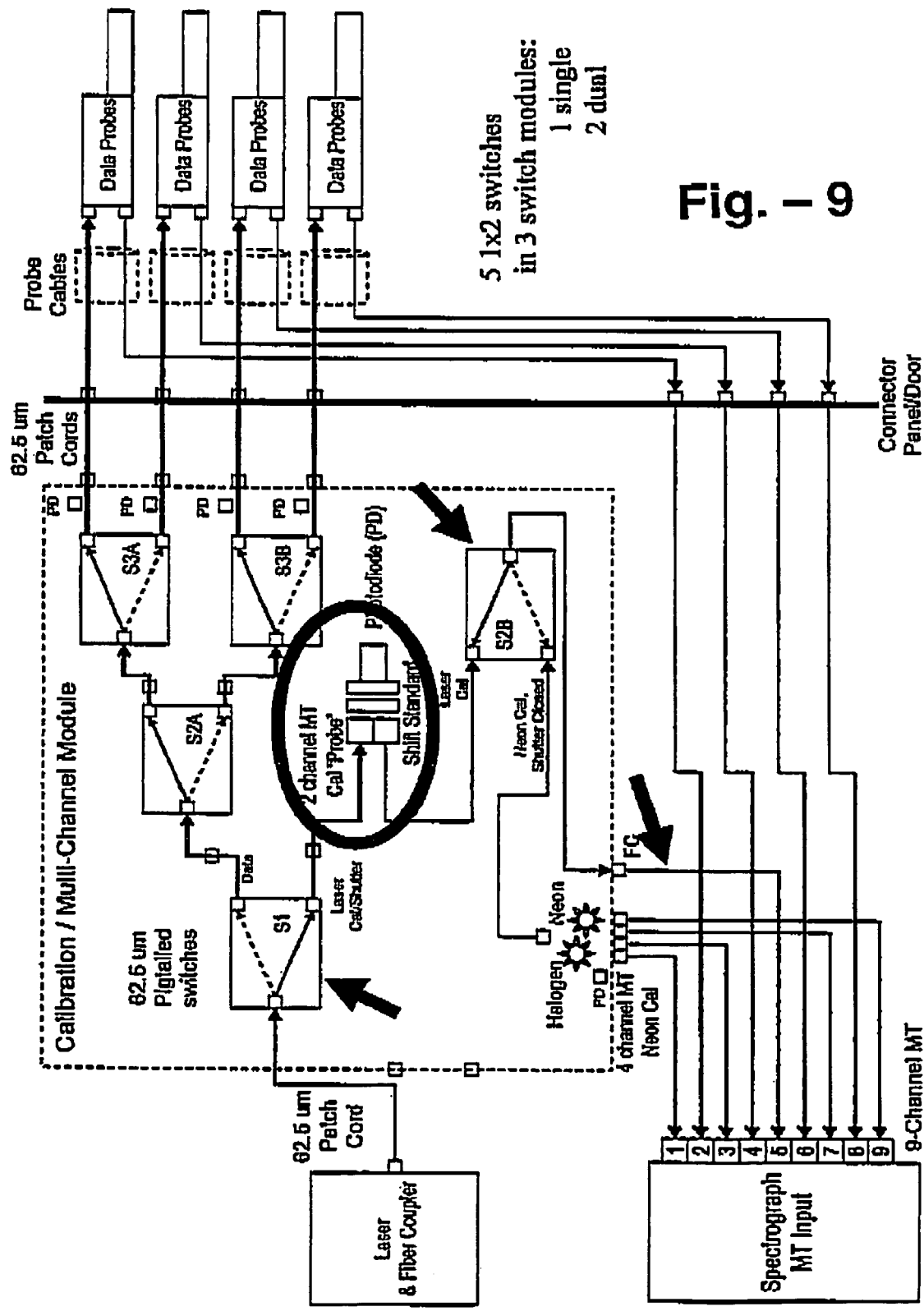
FIG. 9 depicts an internal diamond reference used for laser calibration.

FIG. 8A shows an auto-binning camera image with the five calibration channels illuminated with the halogen lamp of FIG. 7, and FIG. 8B shows how the binning of the four data channels bisects the five calibration channels. System software senses and defines the binning ranges (i.e., the row ranges associated with each channel), and the ranges of FIG. 8B may be computed from the ranges of FIG. 8A, that are sensed using the halogen lamp of FIG. 7.

Figure 11:
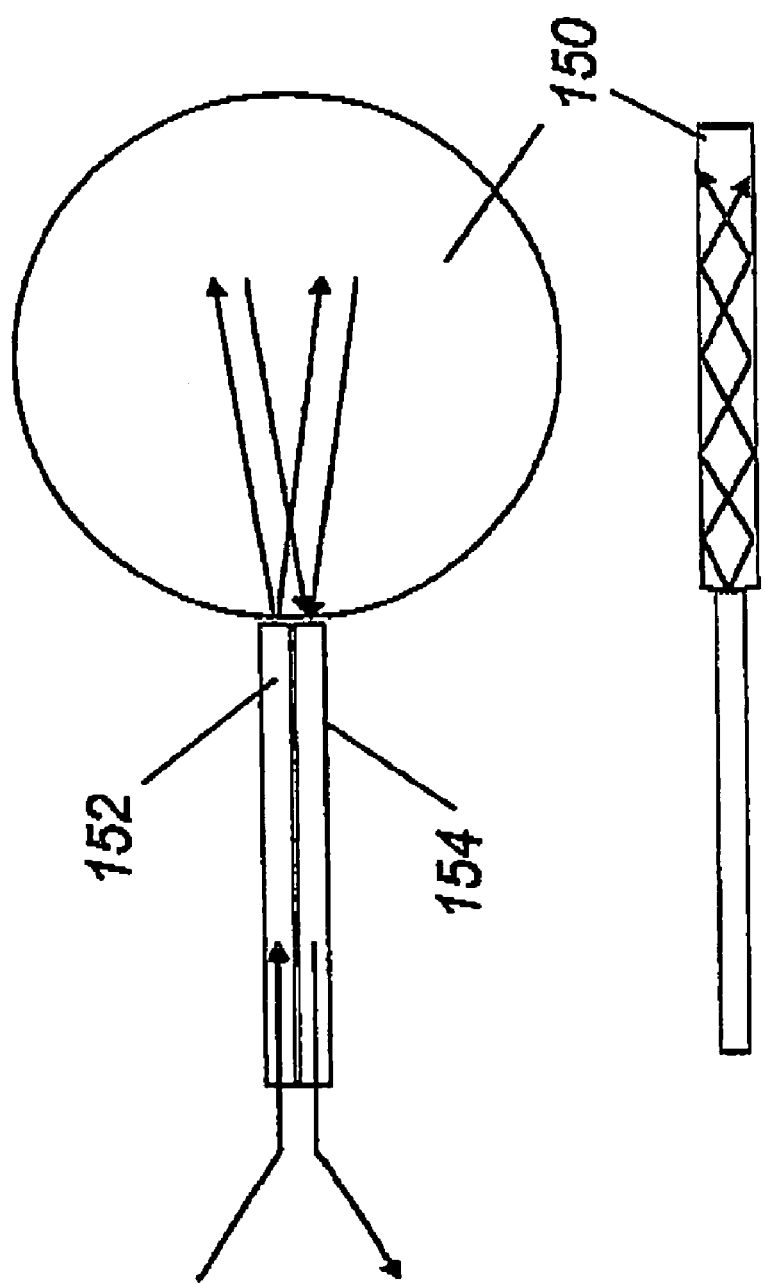
FIG. 11 shows a novel 2-fiber, edge-coupled Raman probe arrangement for diamond laser calibration.

FIG. 9 highlights an area including an internal diamond reference used for laser calibration. In the preferred embodiment, a diamond disc 150 Raman shift reference is used for laser calibration in conjunction with a low-cost, edge-illuminating probe consisting of two unfiltered excitation and collection fibers, 152, 154, as shown in FIG. 11. A commercially available 2-mm diameter×300 micron thick CVD diamond disk is used. As shown in the side view, the waveguiding effect of the edge illumination traps and overlaps excitation and collection paths for effective Raman signal amplification. An excellent diamond signal is obtained without the need for a more expensive filtered Raman probes. No lenses, bandpass filters, notch filters, or beam combiners are required.

Figure 10:
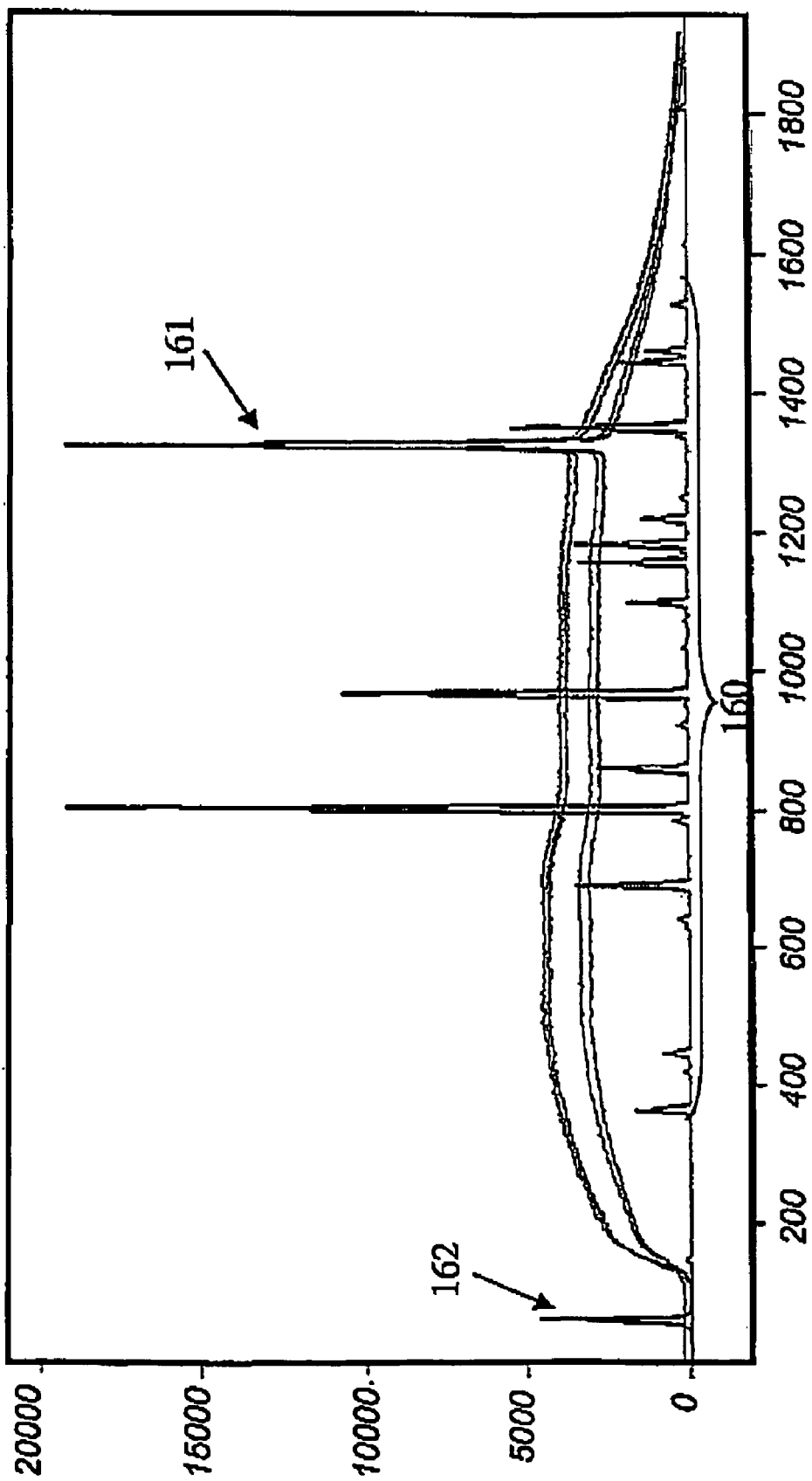
FIG. 10 illustrates CVD diamond samples vs. neon spectra.

FIG. 10 shows the CVD diamond peaks (5 samples) at 161 and neon spectra peaks at 160. Filters in the Raman spectrograph 120 block weak neon calibration lines in spectral region of laser (low Raman shift), thereby limiting the short wavelength extent of neon calibration. On the other hand, the diamond background also overpowers the weak neon lines. However, since the filtered strong laser peak at 162 leaks through the notch filter in the spectrograph, it may be used to augment calibration in the low Raman shift region of the spectrum. The diamond-shifted laser signal lies in the "well-calibrated" range of the spectrograph, allowing accurate determination of the laser wavelength. Thus, the filter leakage of the strong unshifted laser line from the 2-fiber probe, now wavelength-calibrated, can be used to augment the neon calibration, improving accuracy in the very low Raman shift region.

The laser calibration algorithm would then include the following steps:
  Neon calibration of all channels is acquired;
  The laser is diverted to the diamond shift reference by switch S1 and internal probe's excitation fiber 152;
  Diamond Raman signature is collected by the internal probe's collection fiber 154 and routed to the spectrograph's central (or other) calibration channel by switch S2B;
  The spectral position of the diamond-shifted Raman peak is determined per neon spectrograph wavelength calibration;
  The laser wavelength is computed from known Raman shift of diamond; and
  The unshifted laser peak at the lower end of the spectrum is then used to extend the calibration wavelength range.

Figure 12:
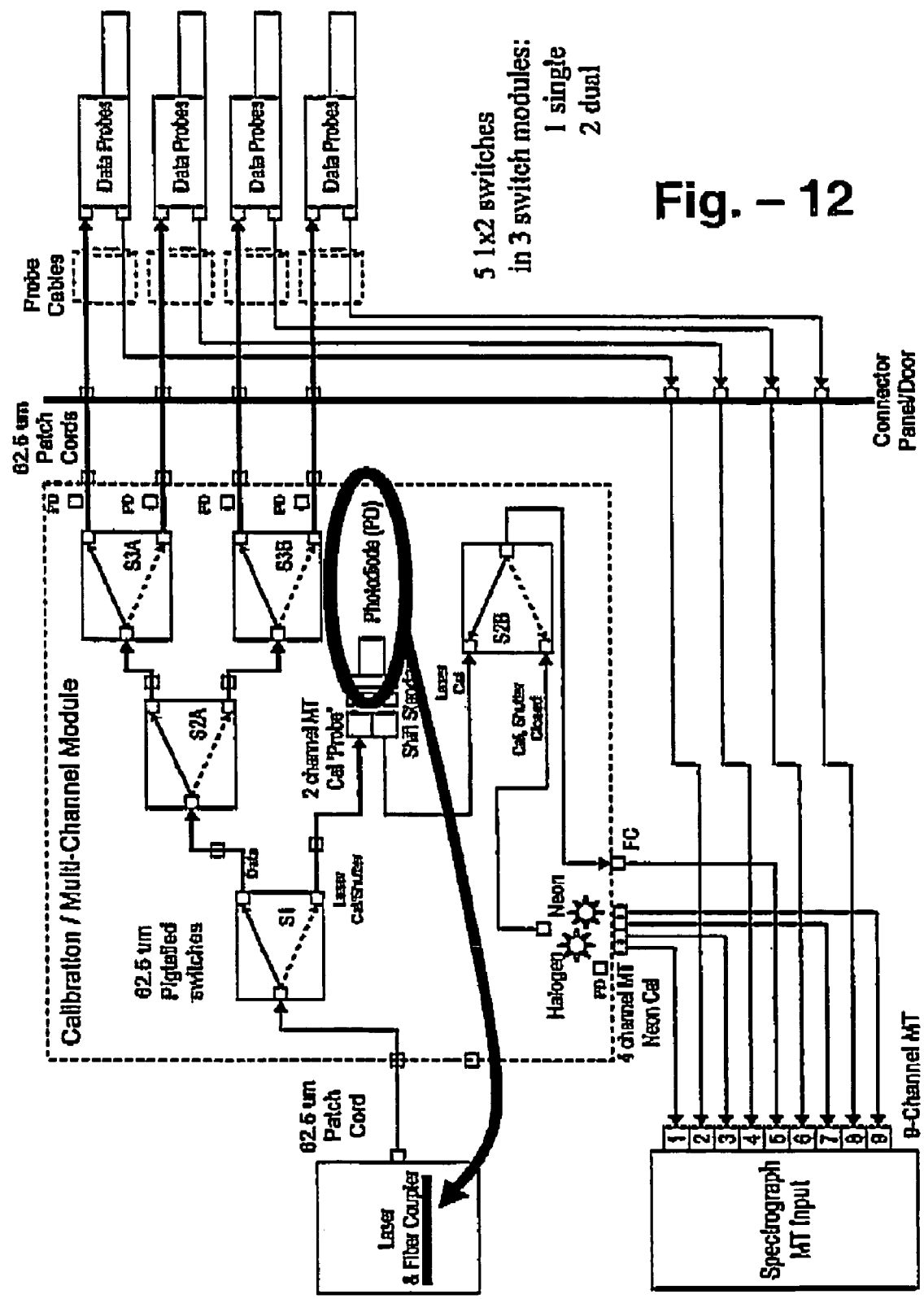
FIG. 12 illustrates automatic fiber coupler alignment, wherein motion servos optimize photodiode signal through a diamond laser calibration path.
Figure 13:
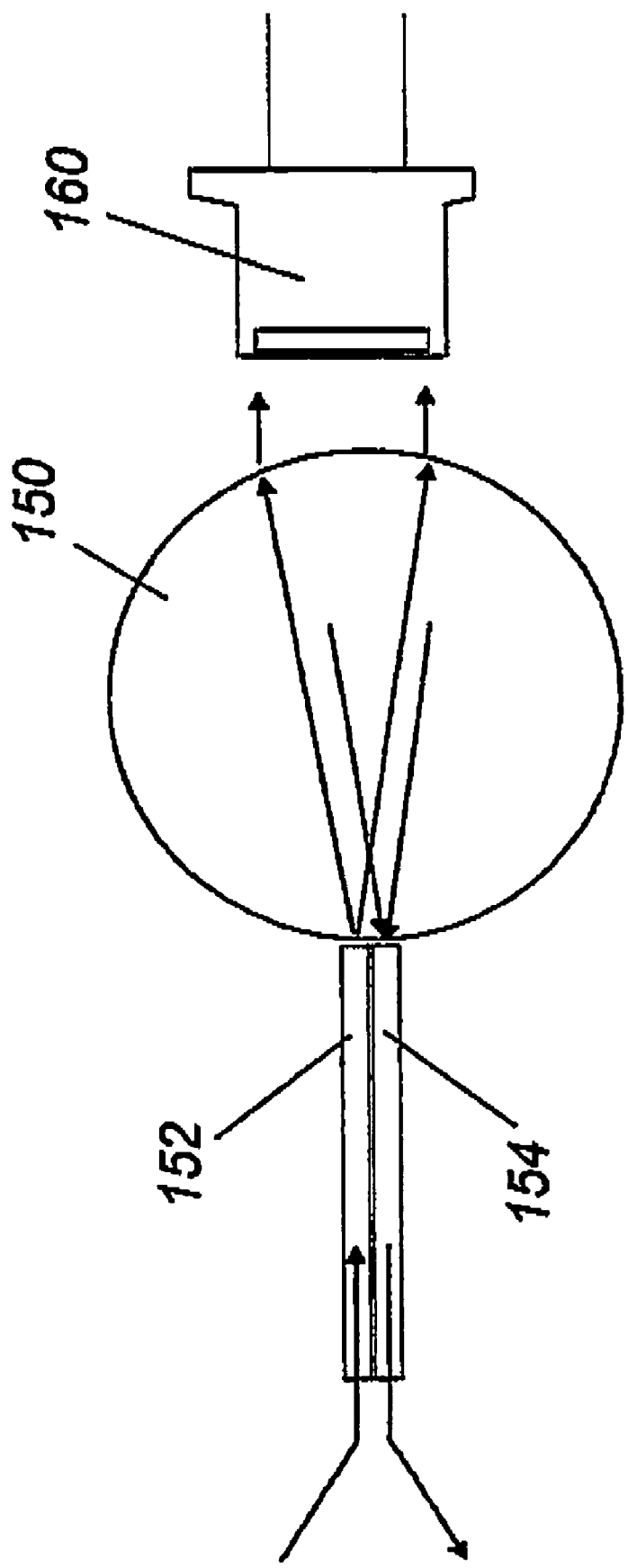
FIG. 13 shows a diamond probe and photodiode arrangement according to the invention.

FIGS. 12 and 13 illustrate yet a further aspect of the invention, namely, the use of an optical feedback signal for automated alignment of the laser/fiber coupler 102. As shown in FIG. 13, a photodiode collects laser light transmitted through the diamond laser cal disk 150, and this is used as a reference. As suggested by FIG. 12, motion servos (not shown) are then used to optimize the photodiode signal to maximize the intensity from the laser/fiber coupler 102.

As a partial summary, the various calibration procedures would include the following steps, though not necessarily in order of performance:
  Data Acquisition:
    Set S1 to DATA
    Set S2 and S3 to select one of the four probes
    Bin for fibers 2,4,6,8
    Neon Lamp must be OFF
  Laser shutter closed:
    Data/Cal switch(es) set to CAL
    Neon Cal/Laser Cal switch (S2) set to Neon Cal
    Neon Lamp OFF
  Neon Calibration:
    Data/Cal switch(es) set to CAL
    Bin for fibers 1,3,5,7,9
    Neon Cal/Laser Cal switch (S2) set to Neon Cal
    Neon Lamp ON
  Laser Calibration:
    Data/Cal switch(es) set to CAL (same binning)
    Neon Cal/Laser Cal switch (S2) set to Laser Cal
    Neon Lamp OFF
  Low Wavenumber calibration:
    Spectrograph notch will block neon calibration near laser
    Rayleigh leakage will be evident during laser cal on fiber 5
    Use Laser cal & Rayleigh line to extend neon cal on fiber 5
    Apply same pixel shift between Rayleigh line and lowest neon line on fibers 1, 3, 7, & 9 to improve their low wavenumber calibration.

Figure 14A:
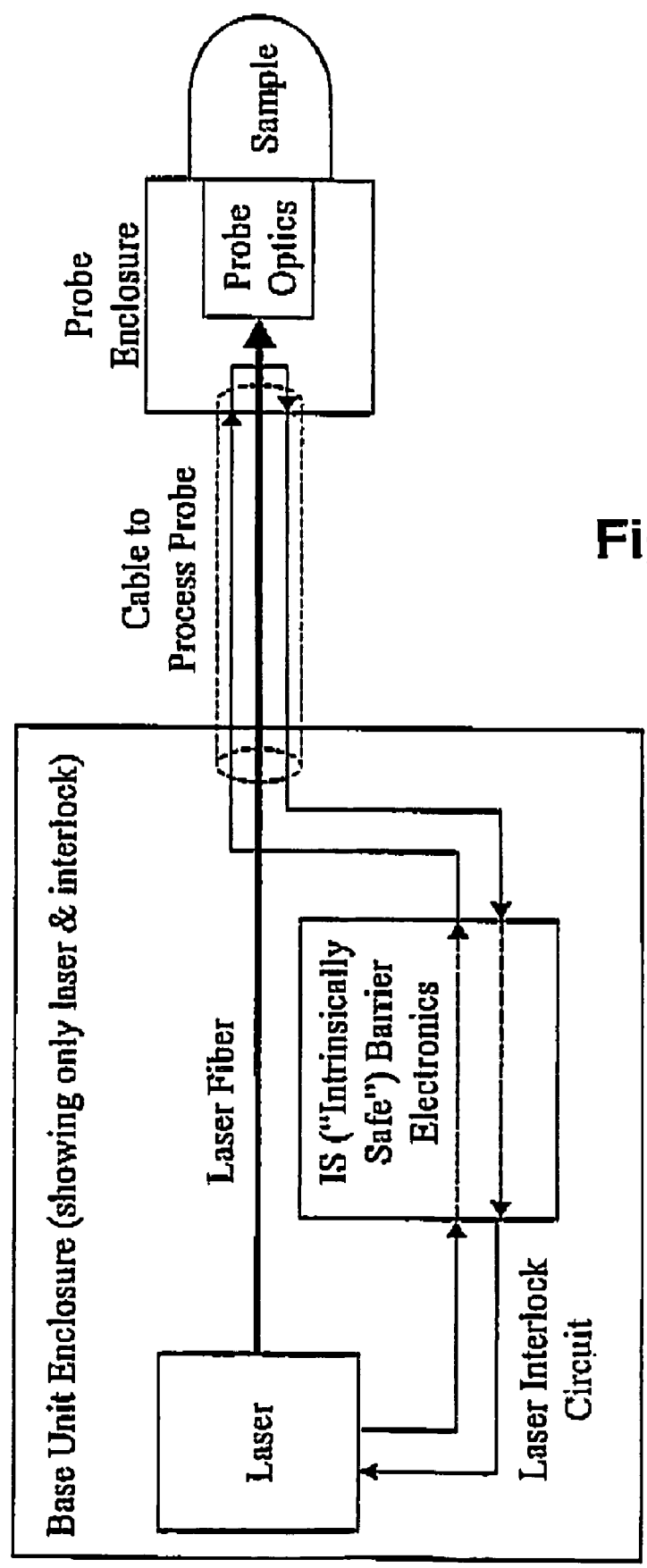
FIG. 14A is a diagram of an inherently safe (IS) interlock.

The preferred embodiments include various other safety features. For example, the fiber cables between the base unit and probe heads carry a pair of wires that function as a laser safety interlock, such that if cable/wires are broken, the laser shuts down. The interlock system shown schematically in FIG. 14A is an existing arrangement designed to use a low voltage/current "intrinsically safe" (IS) circuit certified for use in potentially volatile/explosive industrial environments.

Figure 14B:
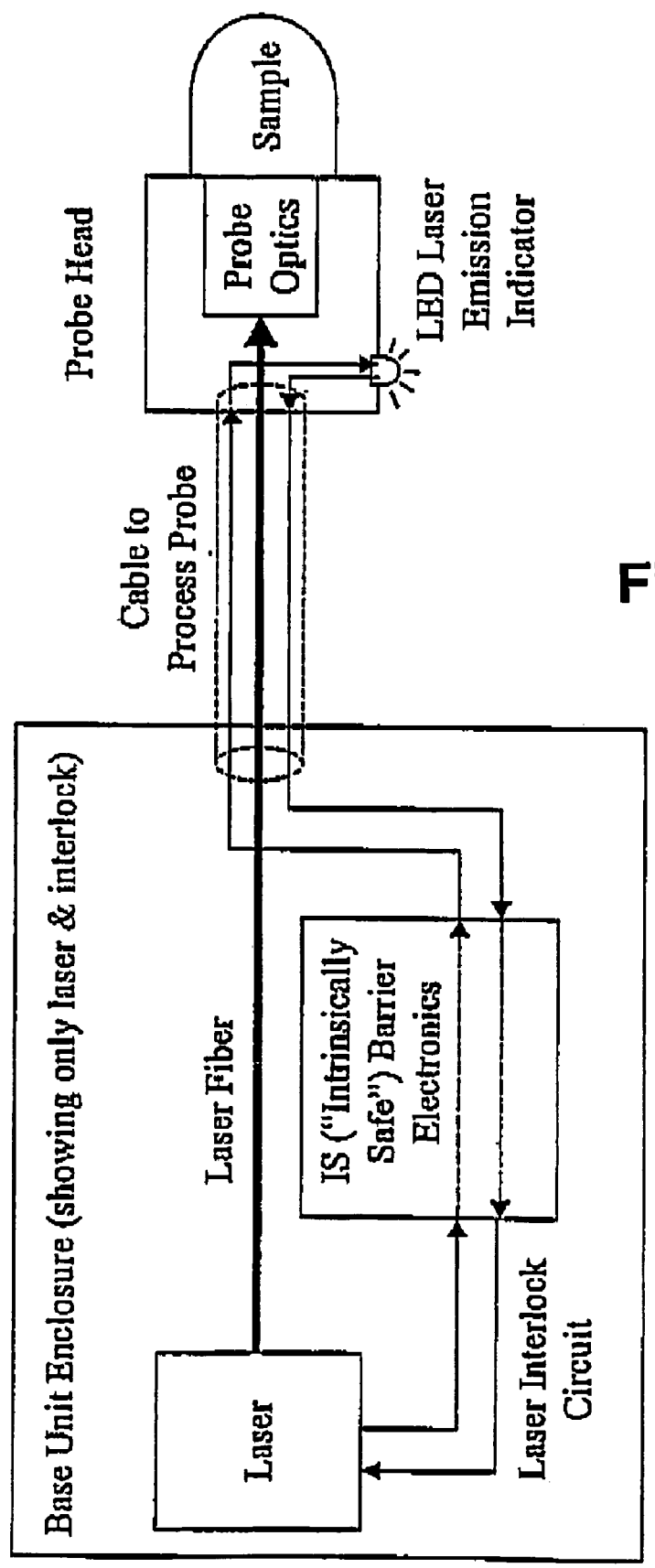
FIG. 14B shows the IS interlock driving a laser emission indicator (EI)

The interlock circuit sources ~8 mA closed circuit and 8V open circuit. According to this invention, the current in the circuit of FIG. 14A is used to power a light-emitting diode (LED), as shown in FIG. 14B, at each probe head for "intrinsically safe" performance. More particularly, the approach is CDRH-compliant (pursuant to personnel safety regulations) "Laser Emission" Indicator and Safety Interlock that is simultaneously IS (pursuant to industrial explosive atmosphere safety regulations). Approaches such as that described in U.S. Pat. No. 6,259,517, incorporated by reference, may alternatively be used.

The system may further accommodate the built-in monitoring of key component integrity using strategically placed photodiodes ("PD" shown in FIG. 1). The detectors are preferably placed at fiber bends to detect light leakage from bent fiber as verification of commanded laser path through fiber switches, and at neon and halogen lamp locations to verify lamp operation.

Figure 15:
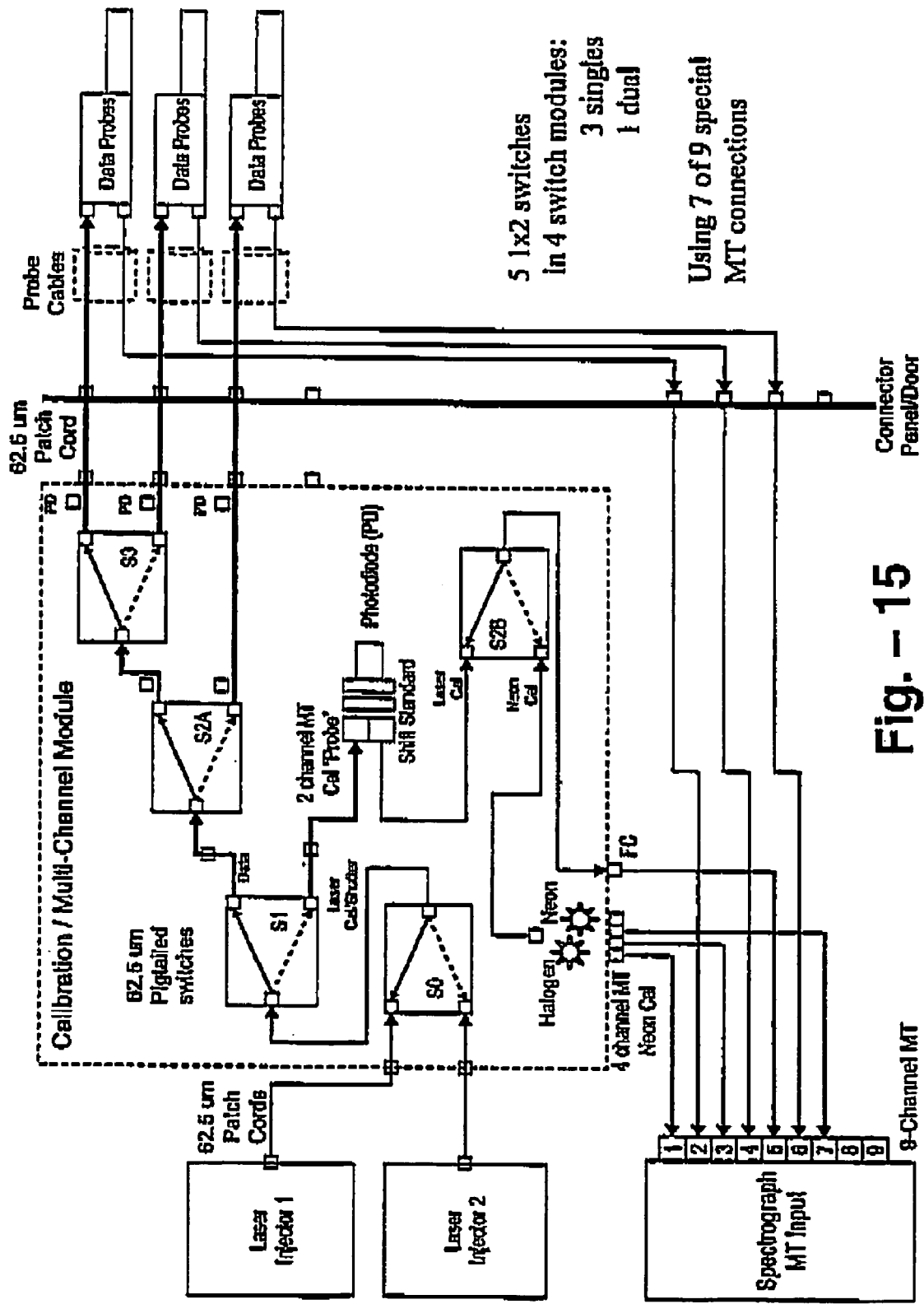
FIG. 15 is a diagram of an alternative embodiment of the invention showing the use of 2 lasers and 3 probes.
Figure 16:
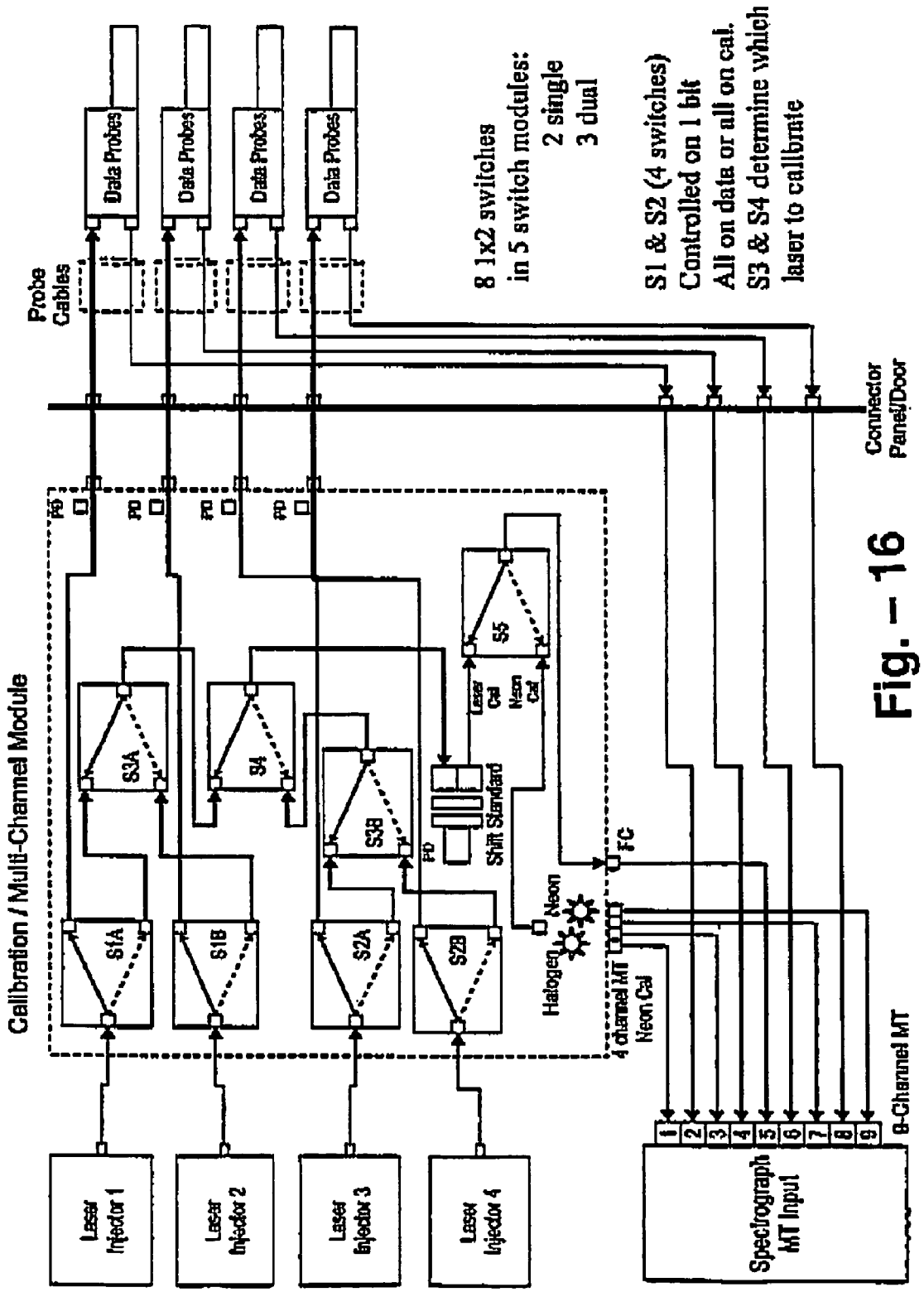
FIG. 16 is a diagram of a further alternative embodiment of the invention showing the use of 4 lasers, 4 probes, and no backup lasers.
Figure 17:
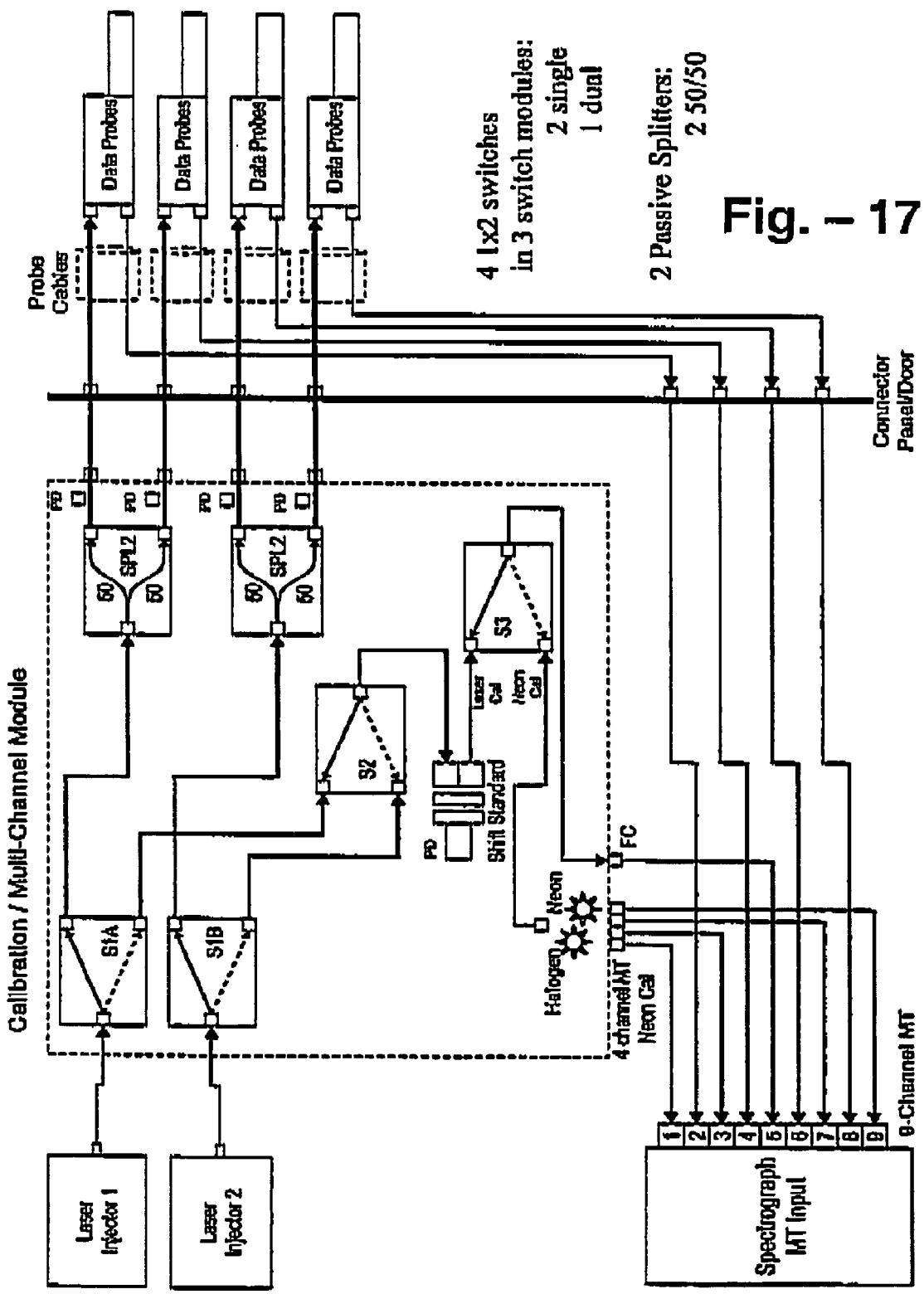
FIG. 17 is a diagram of a different alternative embodiment of the invention showing the use of 2 lasers, 4 probes, passive splitting and no backup.

The concepts described herein may be applied to a wide variety of system configurations in addition to the 4-channel system shown in FIG. 1, including, but not limited to systems with additional laser(s) for hot-swap backup; systems with additional laser(s) for simultaneous vs. sequential multi-channel data acquisition; and systems with single or multiple channel counts other than 4-channels. FIG. 15 is a diagram of an alternative embodiment of the invention showing the use of 2 lasers and 3 probes. FIG. 16 is a diagram of a further alternative embodiment of the invention showing the use of 4 lasers, 4 probes, and no backup lasers. FIG. 17 is a diagram of a different alternative embodiment of the invention showing the use of 2 lasers, 4 probes, passive splitting of the laser to multiple probes without laser backup.

As discussed above, perhaps the best possible calibration is achieved by feeding neon through the actual data fiber to the actual data detectors. However, this in turn requires user intervention or switching of collection channels. FIG. 18 is a diagram depicting an embodiment of the invention using switches from multiple probes facilitating the use of a smaller imager and more direct calibration. In this case, additional switches 180, 182, 184, 186 and 188 are added, enabling the collection fibers from the data probes to be routed to a single-input spectrograph 190, along with inputs from the halogen/neon sources and diamond calibration probe. This allows a single binning area on a shorter CCD to be used for both data collection and calibration. The operation of the switches 180 through 188 would be coordinated with the operation of the switches in the module 110 to carry out the various data-gathering and calibration functions as desired.

We claim:

1. An optical emission analysis system configured for use with a source of excitation energy and a spectrograph including an image sensor having an array of pixels, the system comprising:
   a probe for collecting optical sample data;
   a source of calibration light; and
   optical elements for directing the optical sample data and calibration light to the spectrograph so that adjacent data and calibration channels are formed on the image sensor.

2. The system of claim 1, wherein the optical sample data is representative of a Raman or fluorescence emission.

3. The system of claim 1, wherein each data channel is bounded on either side by an adjacent calibration channel.

4. The system of claim 1, wherein:
   each data channel is bounded on either side by an adjacent calibration channel; and
   interpolation is used between the calibration channels to determine the wavelength calibration of the data channel.

5. The system of claim 1, wherein the optical sample data is dispersed by a plurality of optical gratings such that higher and lower frequency components form different data channels on the image sensor, each adjacent to a calibration channel.

6. The system of claim 1, further including a broadband source of light that may be selectively directed onto the image sensor to directly determine binning ranges of calibration channels.

7. The system of claim 6, wherein the binning ranges or data channels are determined by interpolation of the calibration channel binning.

8. The system of claim 1, further including:
   a plurality of remote optical measurement probes; and
   a plurality of optical switches for routing optical sample data from each probe to the spectrograph on a selective basis.

9. The system of claim 1, further including:
   a plurality of remote optical measurement probes; and
   a plurality of optical switches for routing optical sample data from each probe to the spectrograph on a simultaneous or sequential basis.

10. The system of claim 1, further including:
    a plurality of lasers; and
    optical switches for routing the light from the lasers to the probe on a selective basis.

11. The system of claim 1, wherein the data and calibration channels are tilted relative to the array of pixels.

12. The system of claim 1, further including:
    a laser source: and
    optical switches for:
    a) selectively routing light from the laser source to a material having a known spectral response relative to the laser, and
    b) selectively routing the known spectral response to the spectrograph for use us a laser wavelength calibration channel.

13. The system of claim 12, wherein the optical switches may be configured for use as laser shutter.

14. The system of claim 12, wherein the material having a known spectral response is an edge-illuminated diamond wafer.

15. The system of claim 1, further including optical detectors at points where optical leakage may occur to provide system status or diagnostic information.

16. The system of claim 15, wherein the points where optical leakage may occur include optical fibers with controlled bends.

17. The system of claim 1, further including:
    an intrinsically safe laser interlock circuit carrying a limited current to and from the optical measurement probe using wires cabled with the optical fibers to monitor the integrity of the cable link; and
    an optical illuminator disposed at the location of the probe and connected to the circuit to simultaneously monitor optical path integrity and provide a visual indicator at a probe.

18. An optical emission analysis system configured far use with a source of excitation energy and a spectrograph including an image sensor having an array of pixels, the system comprising:

a probe for collecting optical sample data;

a source of calibration light; a plurality of optical gratings operative to disperse the optical sample data into higher and lower frequency components that form different data channels on the image sensor; and optical elements for directing the calibration light to the spectrograph so that the data channels are between calibration channels.

19. The system of claim 18, wherein the data and calibration channels are tilted relative to the array of pixels.

20. The system of claim 19, further including a broadband source of light that may be selectively directed onto the image sensor to define calibration channel binning.

21. The system of claim 20, wherein the binning ranges or data channels are determined by interpolation of the calibration channel binning.

22. An optical emission analysis system configured for use with a laser source of excitation energy and a spectrograph including an image sensor having an array of pixels, the system comprising:

a probe for collecting optical sample data;

a piece of diamond or other material having a known spectral response relative to the laser, the piece being in the form of a flat sample having opposing surface areas and a peripheral edge with a height substantially smaller that the surface areas; and a source of laser calibration wavelength light derived by illuminating the edge of the sample.

23. The system of claim 22, further including:

a first optical fiber for delivering the excitation energy to the edge of the material; and a second optical fiber for carrying the known spectral response to the spectrograph.

24. The system of claim 22, further including an optical detector in proximity to the reference material for gathering at least a portion of the laser illumination to maximize laser intensity.

25. An optical emission analysis system configured for use with a source of excitation energy and a spectrograph including an image sensor having an array of pixels, the system comprising:

a probe for collecting optical sample data;

a source or calibration light;

optical elements for directing the optical sample data and calibration light to the spectrograph so that multiple channels are formed on the image sensor;

a broadband light source; and one or more optical switches for routing the broadband light onto the image sensor to determine channel binning.

26. The system of claim 25, further including:

a plurality of optical gratings operative to disperse the optical sample data into higher and lower frequency components that form different data channels on the image sensor.

27. The system of claim 26, wherein the data and calibration channels are tilted relative to the array of pixels.

28. The system of claim 25, wherein the data and calibration channels are interleaved.

* * * * *

UNITED STATES PATENT AND TRADEMARK OFFICE
CERTIFICATE OF CORRECTION

PATENT NO.         : 7,158,225 B2
APPLICATION NO. : 10/764319
DATED              : January 2, 2007
INVENTOR(S)        : James M. Tedesco et al.

It is certified that error appears in the above-identified patent and that said Letters Patent is hereby corrected as shown below:

Column 8, line 64, replace "far" with --for--

Column 9, line 2, after "light" move "a plurality of optical gratings" to the beginning of line 3

Signed and Sealed this

Tenth Day of April, 2007

JON W. DUDAS
*Director of the United States Patent and Trademark Office*